United States Patent [19]
Pitkin

[11] Patent Number: 5,376,139
[45] Date of Patent: Dec. 27, 1994

[54] ARTIFICIAL FOOT AND ANKLE

[76] Inventor: Mark R. Pitkin, 32-3 Bayberry Dr., Sharon, Mass. 02067

[21] Appl. No.: 947,919

[22] Filed: Sep. 21, 1992

[51] Int. Cl.$^5$ .............................................. A61F 2/66
[52] U.S. Cl. ........................................ 623/51; 623/49; 623/52; 623/55
[58] Field of Search ................................. 623/50–55, 623/49, 47

[56] References Cited

U.S. PATENT DOCUMENTS

| | | | |
|---|---|---|---|
| 26,753 | 1/1860 | Douglass | 623/53 X |
| 197,943 | 12/1877 | Osborne | 623/53 X |
| 456,206 | 7/1891 | Rowley | 623/55 |
| 854,510 | 5/1907 | Mahaffey | 623/49 |
| 1,090,327 | 3/1914 | Milligan | 623/53 X |
| 5,062,859 | 11/1991 | Naeder | 623/55 |
| 5,139,525 | 8/1992 | Kristinsson | 623/55 |
| 5,156,632 | 10/1992 | Wellershaus | 623/55 |

FOREIGN PATENT DOCUMENTS

| | | | |
|---|---|---|---|
| 0482083 | 2/1917 | France | 623/55 |
| 0790515 | 11/1935 | France | 623/53 |
| 1120697 | 7/1956 | France | 623/53 |
| 0309066 | 11/1918 | Germany | 623/53 |
| 0821529 | 11/1951 | Germany | 623/53 |
| 1134045 | 11/1968 | United Kingdom | 623/55 |
| 1519688 | 11/1989 | U.S.S.R. | 623/55 |
| 8905617 | 6/1989 | WIPO | 623/53 |

*Primary Examiner*—Randall L. Green
*Assistant Examiner*—D. Willse
*Attorney, Agent, or Firm*—Weingarten, Schurgin, Gagnebin & Hayes

[57] ABSTRACT

An artificial ankle and foot is disclosed. The ankle and foot comprise a tibia, a rear-midfoot, and a forefoot (toes), which contact each other at cam surfaces. Extensible elastic ties interconnect the tibia and rear-midfoot and the rear-midfoot and the forefoot. The ties are attached to the respective components at points or zones of attachment which are movable with respect to each other in accordance with the forces acting on the foot and ankle and the rolling motion of the cam surfaces. The relative movement of the zones of attachment alters the tension in the elastic ties, thereby limiting or increasing mobility in the joints between the tibia and rear-midfoot and between the rear-midfoot and the forefoot.

22 Claims, 2 Drawing Sheets

ARTIFICIAL FOOT AND ANKLE

BACKGROUND OF THE INVENTION

The present invention relates to the field of prosthetics, and, in particular, to a biomechanical system designed to assist an amputee in walking, running and other types of locomotion.

I propose to apply a biomechanical emulation of metatarsal and ankle joint movement by incorporation of the necessary mechanical features in the design of the artificial foot and ankle. By mimicking ankle and metatarsal joint movement in the artificial foot, a more normal gait should result. A more natural sequence of the artificial joint's fixation and mobility is proposed.

Preliminary feasibility studies (Pitkin, M. R., Mendelevich, I.A.: "A Prototype of the Rolling Joints Prosthetic Foot", Proc. of the Seventh World Congress of ISPO, Chicago, Ill., Jun. 28–Jul. 3, 1992, p. 134.) indicate that non congruent rolling joint surfaces combined with and held together by linear elastic springs can mimic actual joint motion and provide nonlinear saturation in response to that motion. This investigation was based on the practical evaluation of our previous design (Pitkin M. R., Mendelevich I.A.: "Artificial Foot", Author's Certificate of the USSR No. 820,222, 1981), in which these features have been disclosed. However, the artificial foot in this patent does not provide cam rolling in the ankle zone. It also does not provide sufficient nonlinear saturation of the cam structure, since the points of attachment of the springs in the joint are not movable. In addition, the optimal timing and limits of the fixation/mobility of the prosthetic foot and ankle have not been provided.

In this application, I am using information acquired from the following study by M. R. Pitkin, "New Stride Phases and the Development of Sport Shoe Prototype to Assist the Calf Muscles During Heel-Off", Proc. The 15th Annual Meeting of the American Society of Biomechanics, Tempe, Ariz., 1991, pp. 266–267. This study shows the advantages of optimal timing and "free mobility" intervals in the ankle and metatarsal joints. In this study it was found that during the support phase of the walking stride, after sufficient and almost free mobility of the ankle joint, the calf muscles provide almost total fixation of the ankle joint. Therefore the heel lifts off and the foot begins a rotation around the metatarsal heads. Such rotation is a result of inertia of the body, and the calf muscles lift the heel indirectly by fixation of the ankle.

It is possible to describe the foot-ankle in gait using the following phases:
1) Ankle-Phase (AP);
2) Metatarsal-Phase (MP);
3) Metatarsal-Ankle-Hip-Ankle$_2$-Phase (MAHA$_2$P), where the symbol A$_2$ relates to the ankle of second leg.

The beginning of AP is defined as the moment of toes-off of the rear leg.

The MP starts at the moment of heel-off.

MAHA$_2$P starts from the heel-on and amortization-like, or dampening, plantar flexion of the second leg, which is swinging above the ground during AP and MP. This plantar flexion continues until the foot is positioned on the walking surface.

In each of these phases a human body is representable by a system of one degree of freedom.

It was also noticed that electromyogram studies (EMG) of *musculus gastrocnemius* during a stance period of locomotion (when the foot is in contact with the ground) demonstrated three specific zones, correlated with the phases discussed.

The major activity of *musculus gastrocnemius* takes place at the MP (heel-off). In this phase the ankle angle remains almost unchanged, which indicates a fixation of the joint's mobility. This fact supports the conclusion that lifting of the heel is not by direct muscle-driven plantar flexion, but rather it is a consequence of the inertia of the body. When the second leg touches the ground, phase MAHA$_2$P starts, and the calf muscles of the first leg become involved in a propulsive plantar flexion (a component of the propulsion of the body).

EMG activity of *musculus gastrocnemius* during MAHA$_2$P is significantly less than during the MP. It indicates that the muscle deficit of an amputee can be effectively compensated for by the precise timing and positioning of the passive mechanical resistors.

Firstly, a prosthetic foot has to provide as total a fixation (stopping of mobility) as possible in the ankle joint from the end of the AP and through the MP.

The low level of the EMG of the *musculus gastrocnemius* during the (AP) supports a second requirement for the prosthetic foot and ankle to provide as free as possible mobility in the ankle at this phase.

There is another aspect of the necessity for free mobility in the ankle. In passing from AP to MP during walking with the prosthesis, a patient's stump produces the pair of forces F,-F by its proximal and distal areas. These forces act on the stump's socket and provide the moment about the point of pressure in the metatarsal joint. That moment should be no less than the internal torque, produced by the fore part of the prosthetic foot. The greater the internal torque of resistance, the greater the moment (pair of forces F,-F) produced by the patient's stump. Due to Newton's third law, the forces of the same magnitude act on the stump from the socket. Hence, the greater the internal torque of resistance, the greater the pressure that will be applied to the patient's stump. Clearly, any mechanical means which will decrease such pressure to a stump is highly desirable.

Thus, I conclude that a prosthetic foot has to provide as free a sagittal articulation as possible in the ankle zone during AP and in the metatarsal zone during MP, and as total a fixation as possible in ankle joint from the end of the AP and through the MP.

SUMMARY OF THE INVENTION

In view of the foregoing, it is an object of the present invention to design a prosthetic foot and ankle which provides a more normal dynamic and kinematic pattern of the human walking, running and performing other types of locomotion than seen in previous designs.

It is a further object of the present invention to provide a more normal timing of the mobility in the ankle and metatarsal joints in combination with a minimal resistance to the initiation of the mobility and a nonlinear high resistance to the end of the mobility.

These objects are achieved in accordance with the preferred embodiment of the present invention by including in the design of myself and I. A. Mendelevich ("Artificial Foot," Author's Certificate of the USSR, No. 820,822, 1981) a rear-midfoot simulator and a tibia simulator, in addition to the existing fore and rear foot simulators.

These parts contact each other at cam rolling surfaces, and are connected by extension-type elastic ties, as in the previous design of Pitkin and Mendelevich. In addition, in the present invention, the zones of attachment of the elastic ties are movable to provide an additional control over the tension in the elastic ties.

In accordance with the present invention in operation during locomotion, the first peak of the vertical component of the ground reaction force moves the zones of attachment of the elastic ties between the tibia and the rear-midfoot closer together. This movement decreases the initial tension in these ties and eases the initiation of the mobility in the ankle joint. This convergence of the attachment zones also plays a role of additional shock absorption (amortization or dampening) when the foot stands on the walking surface.

When the vertical component of the ground reaction force decreases, the zones of attachment of the elastic ties between the tibia and the rear-midfoot move away. This increases the resistive torque, which is needed to limit the mobility in the ankle in order to lift the heel and transfer mobility to the metatarsal joint.

The second peak of the vertical component of the ground reaction force decreases the tension in these ties again for initiation of the propulsive plantar flexion. Continuation of the plantar flexion is supported by the elastic moving away of the attachment zones, which increases the returning torque of the ties.

At the same time the second peak of the vertical component of the ground reaction force increases the tension of the ties in the metatarsal joint, which provides an additional propulsive component during toes off.

These and further objects, features and advantages of the present invention will become more obvious from the following description when taken in connection with the drawings which allow, for purpose of illustration only, several embodiments in accordance with the present invention.

DETAILED DESCRIPTION OF THE PREFERRED EMBODIMENTS

Figure 1:
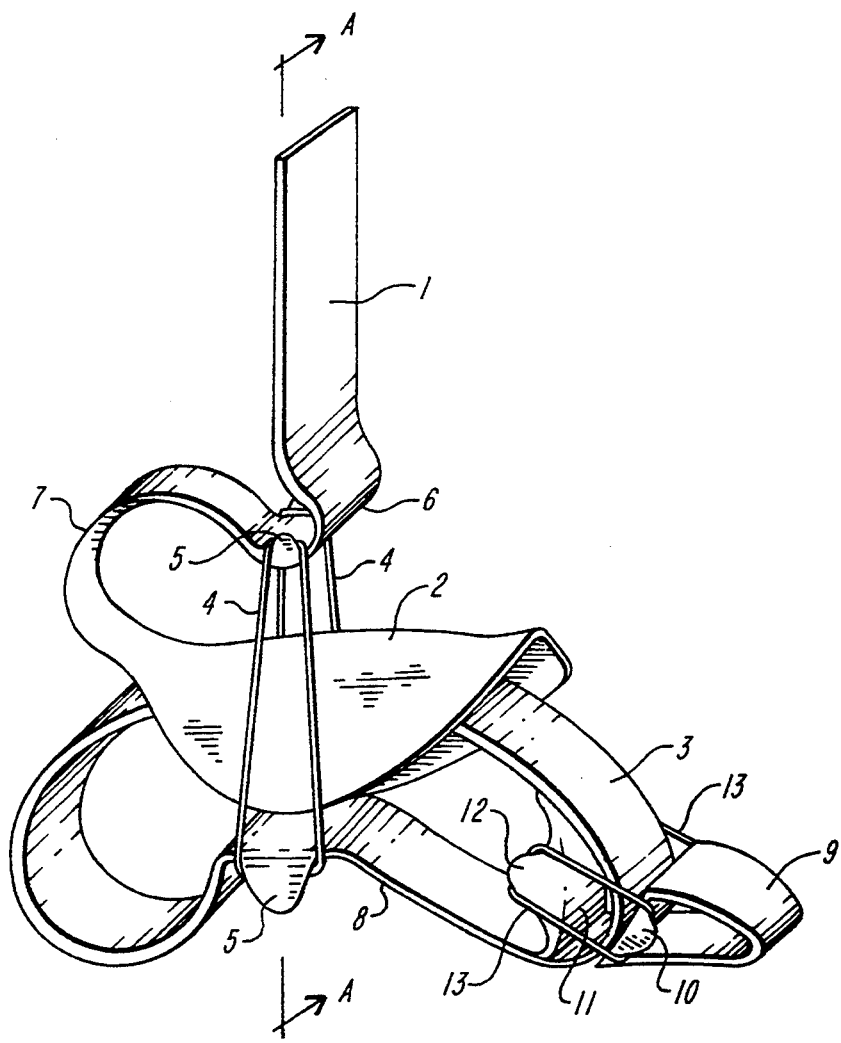
FIG. 1 is a 3-D view of the new prosthetic foot and ankle, wherein an artificial tibia is mounted on an artificial talus part of the rear-midfoot simulator.

With reference to FIG. 1, wherein an artificial tibia 1, having a saddle-like head 2, is mounted on an artificial rear-midfoot 3 by elastic ties 4, which are positioned on hooks 5, it can be seen that tibia's hooks are located on the bottom of a loop 6, which passes smoothly to the loop 7, and the rear-midfoot's hooks are located on the upper of an arch 8.

Figure 2:
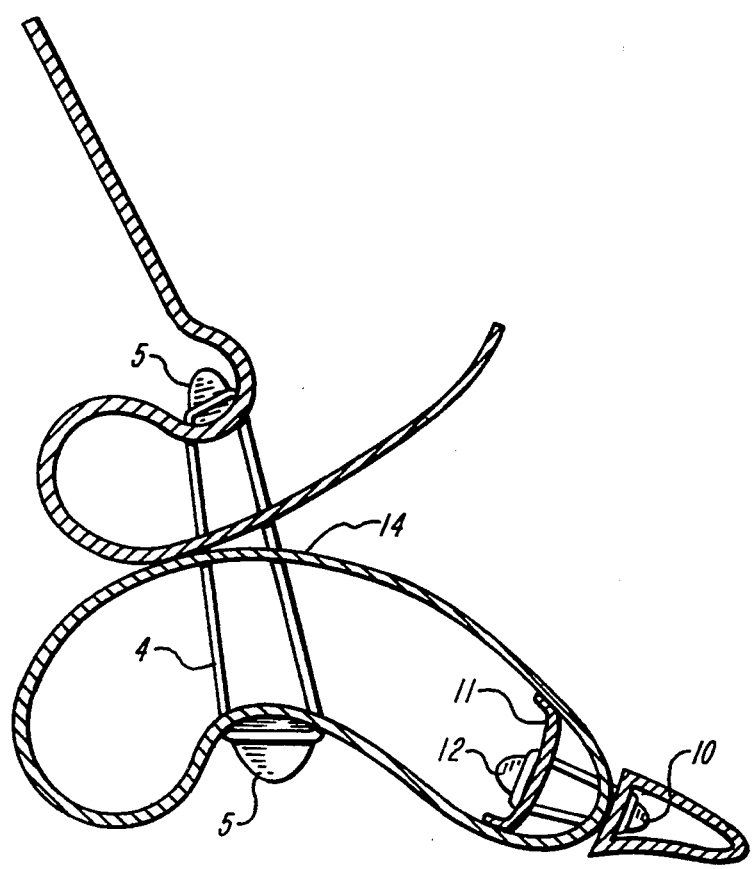
FIG. 2 is a side view, in cross-section, illustrating the ability of the zones of attachment of the ties to move together and move away in the process of cam rolling of the contacting surfaces of the artificial tibia and the artificial talus during the support phase of gait.

The upper part of the tibia 1 is made from an elastic polymer strip, as well as the rear-midfoot 3, which is made as a closed non-circular ring, and has in sagittal cross section a shape of a bean (see also FIG. 2).

Elastic ties 4 are rubber O-rings, the elasticity of which can be provided in accordance with the patient's peculiarities and type of performance.

Forefoot (artificial toes) 9 is made from a polymer strip and has in sagittal cross section a shape of a D-ring with lateral and medial hooks in the zone, which contacts the metatarsal zone of the rear-midfoot 3 and which the radius of curvature is larger than the radius of curvature of the metatarsal zone.

A curved elastic plate 11 is inside the rear-midfoot 3, slightly behind the zone of its contact with forefoot 9 (artificial metatarsal joint) and has lateral and medial hooks 12. The radius of curvature of the plate 11 in sagittal cross section is larger than radius of curvature of the metatarsal zone of the rear-midfoot 3, which can be seen also in FIG. 2.

Hooks 10 and 12 secure lateral and medial rubber O-rings 13. The initial tension of the ties 4 tightens head 2 to the talus's zone 14 (see FIG. 3) of the rear-midfoot 3 and provides stability of the tibia 1 in frontal plane.

Figure 3:
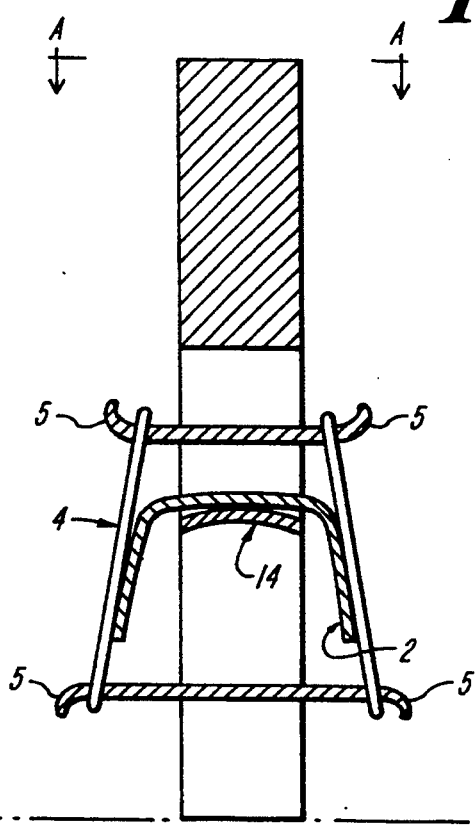
FIG. 3 is a frontal cross section of the drawing in FIG. 1 along line A—A.

As can be seen in FIG. 2 and FIG. 3, the radii of curvature of the head 2 are larger that the radii of curvature of the talus's zone 14 of the rear-midfoot 3 both in sagittal (FIG. 2) and frontal (FIG. 3) planes.

In accordance with the present invention in operation during locomotion, the first peak of the vertical component of the ground reaction force causes the hooks 5 of attachment of the elastic ties 4 between tibia 1 and rear-midfoot 3 to move closer together. It decreases an initial tension in these ties and eases the initiation of the mobility in the ankle joint during AP.

The movement of the attachment zones also plays a role of additional shock absorbtion (amortization or dampening) when the foot interacts with the walking surface (first shock absorbtion is achieved during the dampening of the plantar flexion of the foot, which takes place directly after heel-on).

When the vertical component of the ground reaction force decreases to its minimum, the zones of attachment of the elastic ties (hooks 5 of the tibia 1 and hooks 5 of the rear-midfoot 3 in the arch 8) move away. It increases the resistive torque, provided by ties 4, which is needed to limit the mobility in the ankle in order to lift the heel and transfer mobility to the metatarsal joint.

The second peak of the vertical component of the ground reaction force decreases the tension in these ties again for initiation of the propulsive plantar flexion. Continuation of the plantar flexion is supported by the elastic moving away of the attachment zones, which increases the returning torque of the ties.

At the same time the second peak of the vertical component of the ground reaction force provides a compression of the metatarsal zone of the rear-midfoot 3. It effects a deformation of the plate 11 with hooks 12. Since the radius of curvature of plate 11 is larger than the radius of curvature of the metatarsal zone of the rear-midfoot 3, hooks 12 move closer to the zone of contact with the forefoot 9. It decreases the tension of ties 13 in the metatarsal joint, which makes initiation of the metatarsal deflection during MP easier.

In addition to the cam-rolling effect seen with our previous design, further elastic movement of the hooks 12 away from the hooks 10 increases the tension of the ties 13 and provides an additional propulsive component during $MAHA_2P$ and toes off.

So we can see a self controlled rigidity and biomechanically proved sequence of free and fixed mobility of parts in the present design of an artificial foot and ankle, which have not been achieved in the prior art.

While I have shown and described some embodiments in accordance with the present invention, it is understood that the same is not limited thereto, but is susceptible to numerous changes and modifications as known to those skilled in the art, and I, therefore, do not wish to be limited to the details shown and described herein, but intend to cover all such changes and modifications which are encompassed by the scope of the append claims.

I claim:

1. An artificial foot and ankle comprising:
   a tibia comprising a downwardly facing tibia cam surface and a tibia attachment member including a tibia attachment point;
   a rear-midfoot generally below said tibia comprising an upwardly facing talus cam surface disposed for rolling contact in a talus zone with said tibia cam surface of said tibia, and a midfoot talus zone attachment member including a midfoot attachment point; and
   an extensible elastic talus interconnection between said tibia and said rear-midfoot, said talus interconnection being attached to said tibia at said tibia attachment point of said tibia attachment member and being attached to said rear-midfoot at said midfoot attachment point of said midfoot talus zone attachment member, at least one of said tibia attachment member and said midfoot talus zone attachment member being deformable, whereby distance between said tibia attachment member and said midfoot talus zone attachment member changes in response to a force exerted on said foot and ankle causing a deformation of said at least one of said tibia attachment member and said midfoot talus zone attachment member and in response to rolling motion in the talus zone of said tibia cam surface over said talus cam surface, thereby altering the tension in said extensible elastic talus interconnection.

2. The artificial foot and ankle of claim 1, wherein said rear-midfoot comprises an elastic strip having the form of a closed loop, said talus cam surface being defined by an upper surface of said loop, said midfoot talus zone attachment member being defined by a lower surface of said loop inwardly curved to define an arch, whereby said strip flexes in response to a force exerted thereon.

3. The artificial foot and ankle of claim 2, wherein said midfoot attachment point of said midfoot talus zone attachment member further comprises a hook member located at said arch.

4. The artificial foot and ankle of claim 1, wherein said tibia attachment member comprises a flexible, curved member connected to said tibia cam surface, whereby a force exerted on said tibia moves said tibia attachment member closer to said tibia cam surface by flexion of said curved member.

5. The artificial foot and ankle of claim 4, wherein said flexible, curved member comprises a reversely curved member.

6. The artificial foot and ankle of claim 4, wherein said tibia attachment point of said tibia attachment member further comprises a hook member located on said curved member.

7. The artificial foot and ankle of claim 1, wherein said tibia cam surface of said tibia has a sagittal radius of curvature which is greater than a sagittal radius of curvature of said talus cam surface of said rear-midfoot.

8. The artificial foot and ankle of claim 7, wherein said tibia further comprises lateral and medial arms depending from said tibia cam surface to form a saddle, said saddle having a frontal radius of curvature which is greater than a frontal radius of curvature of said talus cam surface.

9. The artificial foot and ankle of claim 1, wherein:
   said rear-midfoot further comprises an anteriorly facing metatarsal zone cam surface having a convex curvature in sagittal cross-section and a deformable midfoot metatarsal zone attachment member located posteriorly of said metatarsal zone cam surface;
   a forefoot is disposed anteriorly of said rear-midfoot, said forefoot comprising a posteriorly facing forefoot cam surface having a concave curvature in sagittal cross-section and disposed for rolling contact in a metatarsal zone with said metatarsal zone cam surface of said rear-midfoot, said forefoot further comprising a forefoot attachment member; and
   an extensible elastic metatarsal interconnection is disposed between said rear-midfoot and said forefoot, said metatarsal interconnection being attached to said rear-midfoot at said deformable midfoot metatarsal attachment member and being attached to said forefoot at said forefoot attachment member, whereby distance between said deformable metatarsal zone attachment member and said forefoot attachment member changes in response to a force on said rear-midfoot causing a deformation of said deformable metatarsal zone attachment member and in response to rolling motion in the metatarsal zone of said metatarsal zone cam surface over said forefoot cam surface, thereby altering the tension in said extensible elastic metatarsal interconnection.

10. The artificial foot and ankle of claim 9, wherein said extensible elastic talus interconnection and said extensible elastic metatarsal interconnection each comprise a medial and a lateral elastic O-ring.

11. The artificial foot and ankle of claim 9, wherein said tibia attachment member, said midfoot talus zone attachment member, said midfoot metatarsal zone attachment member, and said forefoot attachment member each further comprise a pair of medially and laterally disposed hooks configured to receive corresponding ones of said medial and lateral O-rings.

12. The artificial foot and ankle of claim 9, where said forefoot comprises a closed loop polymer strip having a generally D-shaped form in sagittal cross-section.

13. The artificial foot and ankle of claim 9, wherein said forefoot cam surface has a sagittal radius of curvature larger than a sagittal radius of curvature of said metatarsal zone cam surface of said rear-midfoot.

14. The artificial foot and ankle of claim 9, wherein said deformable metatarsal zone attachment member of said rear-midfoot comprises a curved deformable elastic plate located slightly posteriorly of said metatarsal zone cam surface, said plate having a sagittal radius of curvature larger than the sagittal radius of curvature of said metatarsal zone cam surface.

15. The artificial foot and ankle of claim 1, further comprising a deformable forefoot disposed anteriorly of said rear-midfoot.

16. An artificial foot and ankle comprising:
   a tibia comprising a downwardly facing tibia cam surface;

a rear-midfoot comprising an upwardly facing talus cam surface disposed for rolling contact in a talus zone with said tibia cam surface of said tibia;

means formed with at least one of said tibia and said rear-midfoot for deforming in response to a force exerted on said foot and ankle; and means interconnecting said tibia and said rear-midfoot comprising an extensible elastic talus interconnection for providing a restoring force between said tibia and said rear-midfoot in response to rolling motion in the talus zone of said tibia cam surface over said talus cam surface and in response to deformation of said deforming means due to a force exerted on said foot and ankle.

17. The artificial foot and ankle of claim 16, wherein said deforming means comprises a deformable attachment member on said tibia to retain said extensible elastic talus interconnection.

18. The artificial foot and ankle of claim 17, wherein said deformable attachment member on said tibia comprises an elastic strip having the form of a loop.

19. The artificial foot and ankle of claim 18, wherein said deformable attachment member further comprises a hook member.

20. The artificial foot and ankle of claim 16, wherein said deforming means comprises a deformable attachment member on said rear-midfoot to retain said extensible elastic talus interconnection.

21. The artificial foot and ankle of claim 20, wherein said deformable attachment member on said rear-midfoot comprises an elastic strip having the form of an upwardly curved arch.

22. The artificial foot and ankle of claim 21, wherein said deformable attachment member further comprises a hook member.

* * * * *